United States Patent [19]

Bergot

[11] Patent Number: 5,183,885
[45] Date of Patent: Feb. 2, 1993

[54] METHOD FOR CHROMATOGRAPHIC SEPARATION OF SYNTHETIC PHOSPHOROTHIOATE OLIGONUCLEOTIDES

[75] Inventor: B. John Bergot, Redwood City, Calif.

[73] Assignee: Applied Biosystems, Inc., Foster City, Calif.

[21] Appl. No.: 779,012

[22] Filed: Oct. 18, 1991

[51] Int. Cl.$^5$ .................... C07B 63/00; C07H 21/04; C07H 1/06
[52] U.S. Cl. ................ 536/25.41; 536/55.3; 536/27.12; 935/19
[58] Field of Search .......... 536/27, 28, 29, 55.3; 935/19

[56] References Cited

PUBLICATIONS

LaPlanche et al., Nucleic Acids Research, vol. 14, pp. 9081-9093 (1986).
Haddad and Jackson, Ion Chromatography (Elsevier, Amsterdam, 1990), pp. 1-25, 29-47, and 195-207.
Pearson, J. Amer. Chem. Soc., vol. 85, pp. 3533-3539 (1963).
Chemical Abstracts 112(11):94794t. Maisano et al. Bio-Chromatography 4(5):279-281, 1989.
Matsukura et al. Proc. Natl. Acad. Sci. 84:7706-7710, 1987.

*Primary Examiner*—John W. Rollins
*Assistant Examiner*—Gary L. Kunz
*Attorney, Agent, or Firm*—Stephen C. Macevicz

[57] ABSTRACT

A method is provided for the preparation and/or analysis or synthetic phosphorothioate and -dithioate oligonucleotides. In particular, the method permits separation of fully sulfurized phosphorothioate or -dithioate oligonucleotides from incompletely sulfurized defect species on strong-anion exchange HPLC columns using concentration gradients of novel "soft base" anionic eluents, such as bromide, thiocyanate, and the like.

6 Claims, 3 Drawing Sheets

METHOD FOR CHROMATOGRAPHIC SEPARATION OF SYNTHETIC PHOSPHOROTHIOATE OLIGONUCLEOTIDES

FIELD OF THE INVENTION

The invention relates generally to the preparation and/or analysis of synthetic phosphorothioate and -dithioate oligonucleotides, and more particularly, to a method for separating fully sulfurized phosphorothioate or -dithioate oligonucleotides from incompletely sulfurized defect species by strong-anion exchange high performance liquid chromatography (HPLC).

BACKGROUND

Anti-sense oligonucleotides are being developed to treat a variety of diseases, particularly viral infections, e.g. Matsukura et al, Proc. Natl. Acad. Sci., Vol. 86, pgs. 4244–4448 (1989). An antisense oligonucleotide is a synthetic oligonucleotide of varying length, usually in the range of about 12 to 30 nucleotides, or nucleotide analogs, whose sequence is complementary to a predetermined segment of RNA, either freshly transcribed or messenger (mRNA), associated with some foreign or otherwise inappropriately expressed gene. It is believed that when an antisense oligonucleotide hybridizes to its target RNA, it either blocks translation or processing of the RNA or makes it susceptible to enzymatic degradation. One problem with this approach has been the difficulty of getting the antisense oligonucleotide to its target RNA in sufficient concentration and for sufficient duration to be effective in shutting down the synthesis of undesired proteins, e.g. viral enzymes, coat proteins, and the like. The susceptibility of the phosphodiester linkage of the oligonucleotides to nuclease digestion is believed to be an important cause of this difficulty, and has prompted the development of a variety of nucleoside oligomers linked by nuclease-resistant analogs of the natural phosphodiester bond, e.g. Miller et al, U.S. Pat. No. 4,511,713 and Ts'o U.S. Pat. No. 4,469,863 (methyl- and arylphosphonates); Miro et al, Nucleic Acids Research, Vol. 17, pgs. 8207–8219 (1989) (phosphoroselenoates); Brill et al, J. Am. Chem. Soc., Vol. 111, pg. 2321 (1989)(phosphorodithioates); and Matsukura et al, Proc. Natl. Acad. Sci., Vol. 84, pgs. 7706–7710 (1987), and Gene, Vol. 72, pgs. 343–347 (1988) (phosphorothioates).

The phosphorothioate and phosphorodithioate analogs are especially promising because they are highly nuclease-resistant, have the same charge as natural oligonucleotides, and are taken up by cells in effective amounts.

Phosphorothioates can be synthesized by automated DNA synthesizers using hydrogen phosphonate or phosphoramidite chemistries. In the former approach, the phosphonate backbone can be sulfurized in a single step off of the automated synthesizer after synthesis. This is advantageous because the phosphonate moieties are sulfurized by exposure to elemental sulfur dissolved in an organic solvent. Since the sulfur readily precipitates out of solution, the off-column sulfurization avoids costly blockages of valves and tubing of the synthesizer by sulfur precipitates. A drawback of this route of phosphorothioate synthesis is that coupling yields during chain elongation are typically lower than those obtained using phosphoramidite chemistry, Gaffney and Jones, Tett. Lett., Vol. 29, pgs. 2619–2622 (1988). The practical importance of high coupling yields is demonstrated by the synthesis of a 28-mer where a 99% coupling yield per step results in an overall yield of 76% ($0.99^{27}$), whereas a 96% yield per step results in an overall yield of only 33% ($0.96^{27}$).

Phosphoramidite chemistry, with coupling yields typically greater than 99%, is presently the more desirable approach to phosphorothioate and phosphorodithioate synthesis. However, the phosphite intermediates, which would be sulfurized, are unstable under the conditions of the detritylization step of the reaction cycle. Thus, the phosphite linkage must be sulfurized after each coupling step. This can be accomplished with a variety of sulfurizing agents, e.g. Matsukura et al, Gene (cited above)(elemental sulfur); Iyer et al, J. Org. Chem., Vol. 55, pgs. 4693–4699 (1990)(a thiosulfonate sulfurizing agent); Hirschbein, U.S. patent application Ser. No. 07/464,182 (thiuram disulfide and polysulfide sulfurizing agents); and Stec et al, U.S. patent application Ser. No. 07/512,644 (thiophosphorus sulfurizing agents). Unfortunately, none of these agents provides 100% sulfurization. At each sulfurization step a small fraction of the phosphite precursors are oxygenated instead of sulfurized. This leads to the synthesis of a complex mixture of phosphorothioate oligonucleotides with respect to the number and distribution of oxygens along the phosphodiester backbone. The fraction of a product containing a given number of oxygens follows the binomial distribution. For example, in the synthesis of a 20-mer phosphorothioate oligonucleotide where the sulfurization yield is 99% at each step, the fraction of the product with, say, 1 and 2 oxygenations in place of sulfurizations is given by the second and third terms, respectively, of the binomial expansion of $(0.99+0.01)^{20}$, or $\binom{20}{1}(0.99)^{19}(0.01)=0.165$ and $\binom{20}{2}(0.99)^{18}(0.01)^2=0.016$, respectively. Thus, relatively large fractions of even modestly sized phosphorothioate oligonucleotides are incompletely sulfurized and, because of physiochemical similarity of the completely and incompletely sulfurized compounds, separation and/or analysis of the two species has proven to be inconvenient, usually requiring NMR analysis, or like procedures.

In view of the desire to employ phosphorothioate and phosphorodithioate analogs of oligonucleotides as pharmaceutical compounds, it would be advantageous to have available methods for preparation and analysis of the sulfurized products that would permit separation of fully sulfurized species from partially sulfurized species and that would permit a convenient and inexpensive way of monitoring yields of completely sulfurized analogs, particularly in connection with phosphoramidite and/or phosphorthioamidite chemistries.

SUMMARY OF THE INVENTION

The invention is directed to a method for separating fully sulfurized phosphorothioate and/or -dithioate oligonucleotides from partially sulfurized species by strong anion exchange high performance liquid chromatography (HPLC). The method comprises the steps of (1) impregnating a strong anion exchanger with a mixture of completely sulfurized and incompletely sulfurized phosphorothioate or phosphorodithioate oligonucleotides, (2) passing a buffer solution through the strong anion exchanger wherein the buffer solution comprises a concentration of a soft-base counter ion which monotonically increases with time to a sample-desorbing concentration; and (3) recovering the eluate from step (2) containing the completely sulfurized phosphorothioate or phosphorodithioate oligonucleotide. The invention also forms the basis for a rapid and convenient method for analyzing the degree of sulfurization of phosphorothioate oligonucleotides which uses far less sample than other currently available techniques.

As used herein "soft-base counter ion" means a base suitable for displacing a phosphorothioate moiety from a cationic group on a strong anion exchanger, and more particularly, it refers to an electronegative, polarizable base which is chemically stable in the reagents and pH of the buffer solution, and which has negligible absorbance in the range of 250-280 nm. Guidance for selecting soft bases is given by Pearson, in J. Amer. Chem. Soc., Vol. 85, pgs. 3533-3539 (1963). Exemplary soft-base counter ions include bromide, thiocyanate, iodide, azide, and sulfide. Preferably, the soft base is selected from the group consisting of bromide and thiocyanate.

As used herein the term "sample-desorbing concentration" in reference to the soft-base counter ion means a concentration of a soft-base counter ion that is sufficient to elute a fully sulfurized phosphorothioate or -dithioate oligonucleotide from a strong anion exchanger. This concentration depends on the type of soft-base counter ion, the type of the cationic group on the exchanger, the organic modifier employed, pH, the length of the phosphorothioate or -dithioate oligonucleotides in the sample, and other similar parameters. The sample-desorbing concentration is readily determined for particular embodiments by routine experimentation.

The term "oligonucleotide" as used herein includes linear oligomers of natural or modified nucleosides or of non-nucleosidic analogs linked by phosphodiester bonds or analogs thereof ranging in size from a few monomeric units, e.g. 2-3, to several several tens of monomeric units, e.g. 30-50. In particular, the term includes non-natural oligomers having phosphorous-containing linkages whose phosphorous(III) precursors are amenable to sulfurization, e.g. Takeshita et al, J. Biol. Chem., Vol. 282, pgs. 10171-10179 (1987); and Eapienis et al, pgs. 225-230 in, Bruzik and Stec, eds., *Biophosphates and Their Analogs—Synthesis, Structure, Metabolism, and Activity* (Elsevier, Amsterdam, 1986).

As used herein, "incompletely sulfurized" in reference to phosphorothioate or -dithioate oligonucleotide means that one or more of the non-bridging oxygens of one or more of the phosphodiester linkages have failed to be replaced with sulfur. Conversely, "completely sulfurized" in reference to phosphorothioate or -dithioate oligonucleotide means that one (-thioate) or both (-dithioate) of the non-bridging oxygens of every phosphodiester linkage have been replaced with sulfur.

S-d($C_{12}G_5T_{10}$).

wherein (for example) d($C_{12}G_5T_{10}$) represents a 27-mer oligodeoxyribonucleotide 5'- CCCCCCCCCCCCGGGGGTTTTTTTTTT and the prefix "S-" indicates that the phosphodiester linkages have been sulfurized.

Figure 1A:
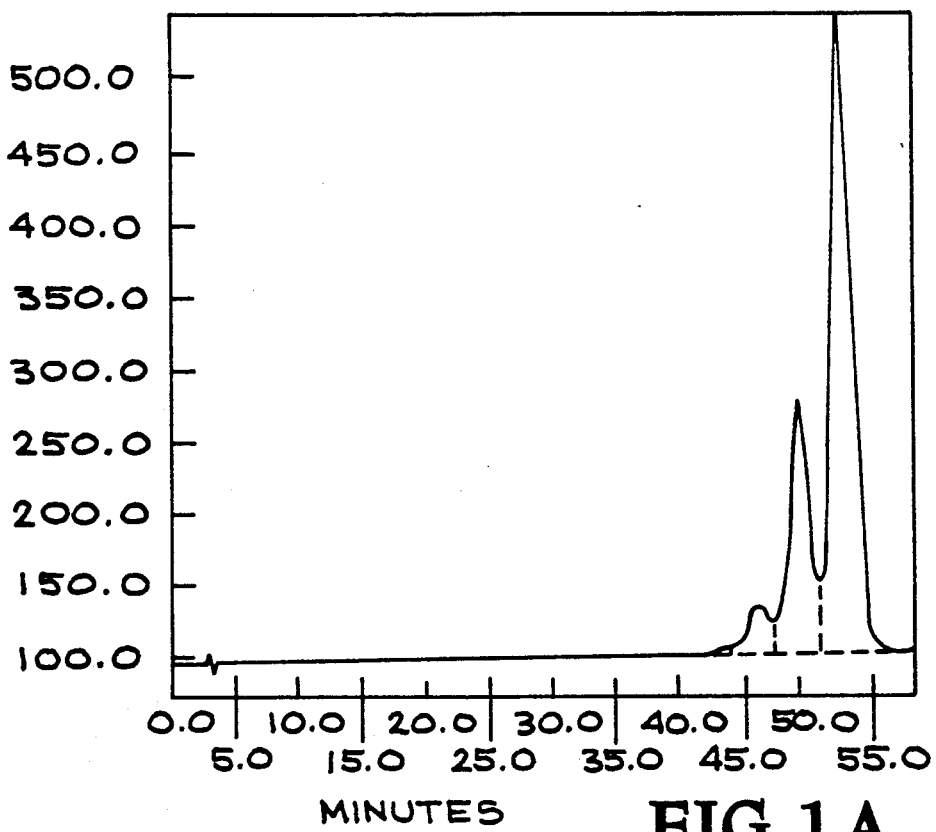
FIG. 1a is a chromatogram of compound (1)
Figure 1B:
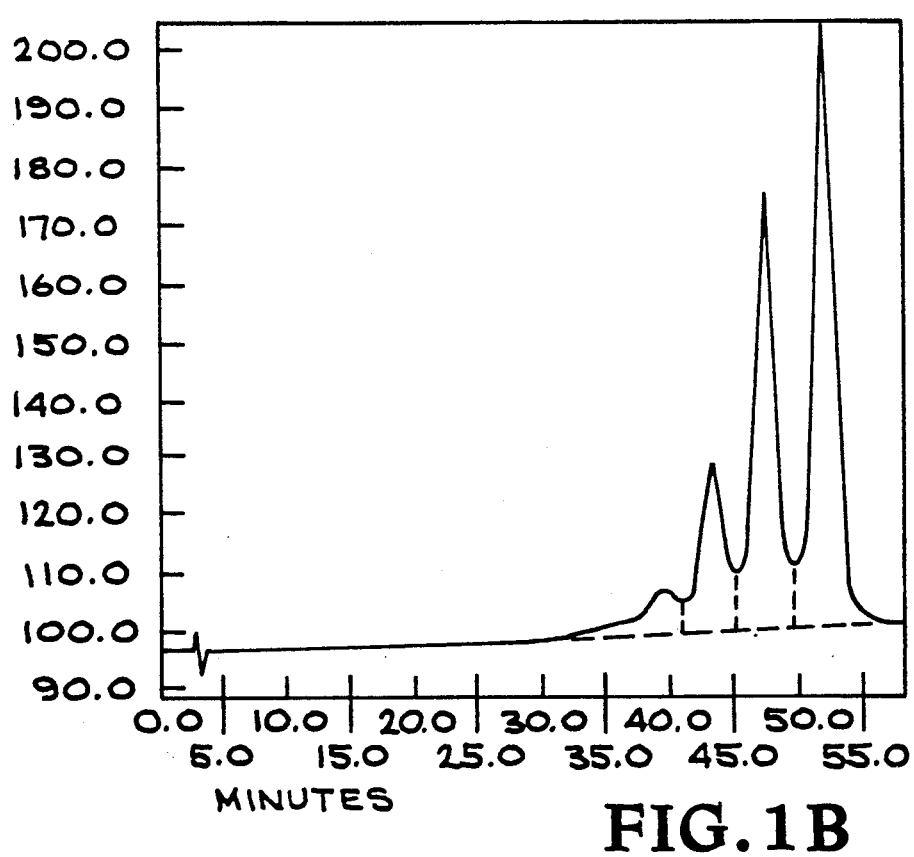

FIG. 1b is a chromatogram of compound (2) high O:

S-d($A_3C_7G_7T_4$).

Figure 1C:
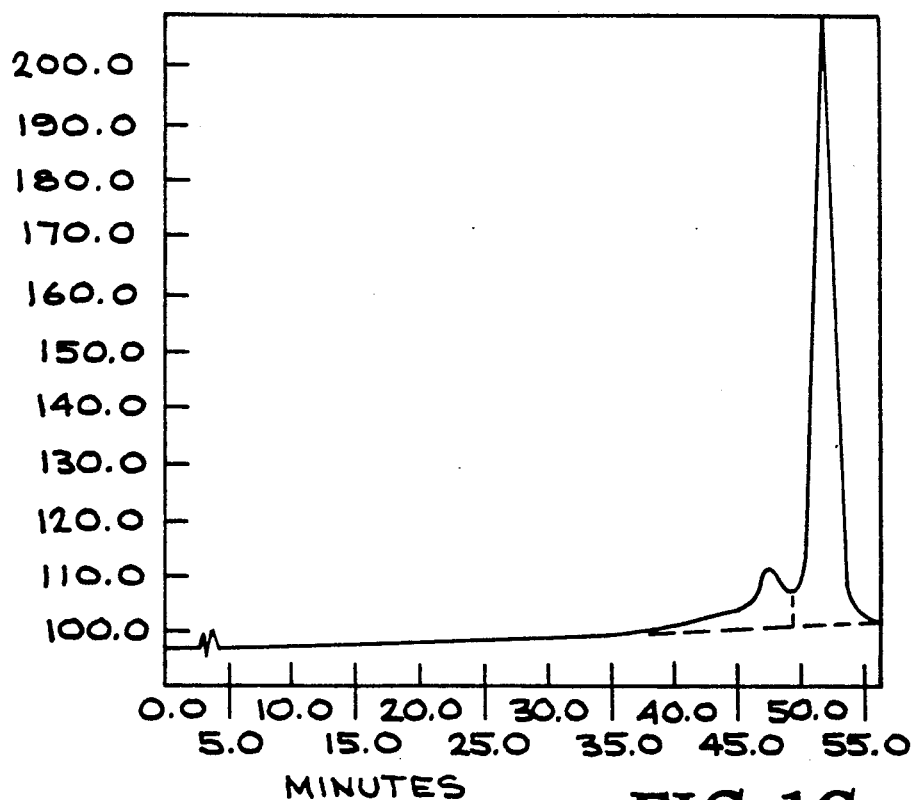

FIG. 1c is a chromatogram of compound (2) low O:

S-d($A_3C_7G_7T_4$).

Figure 1D:
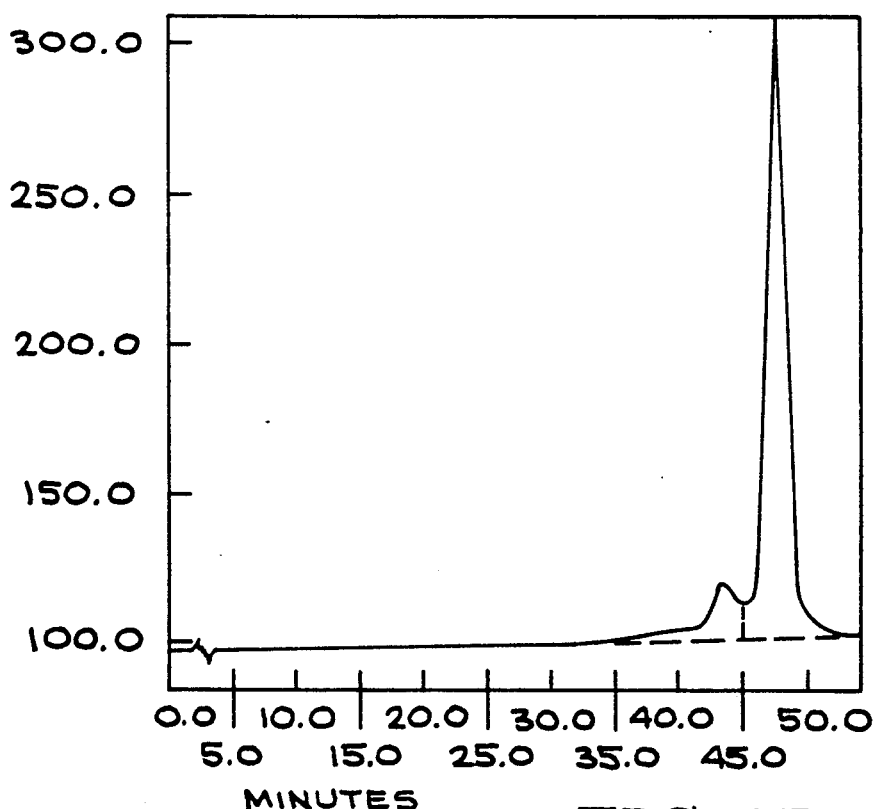

FIG. 1d is a chromatogram of compound (3):

S-d($A_1C_8G_2T_9$).

Figure 1E:
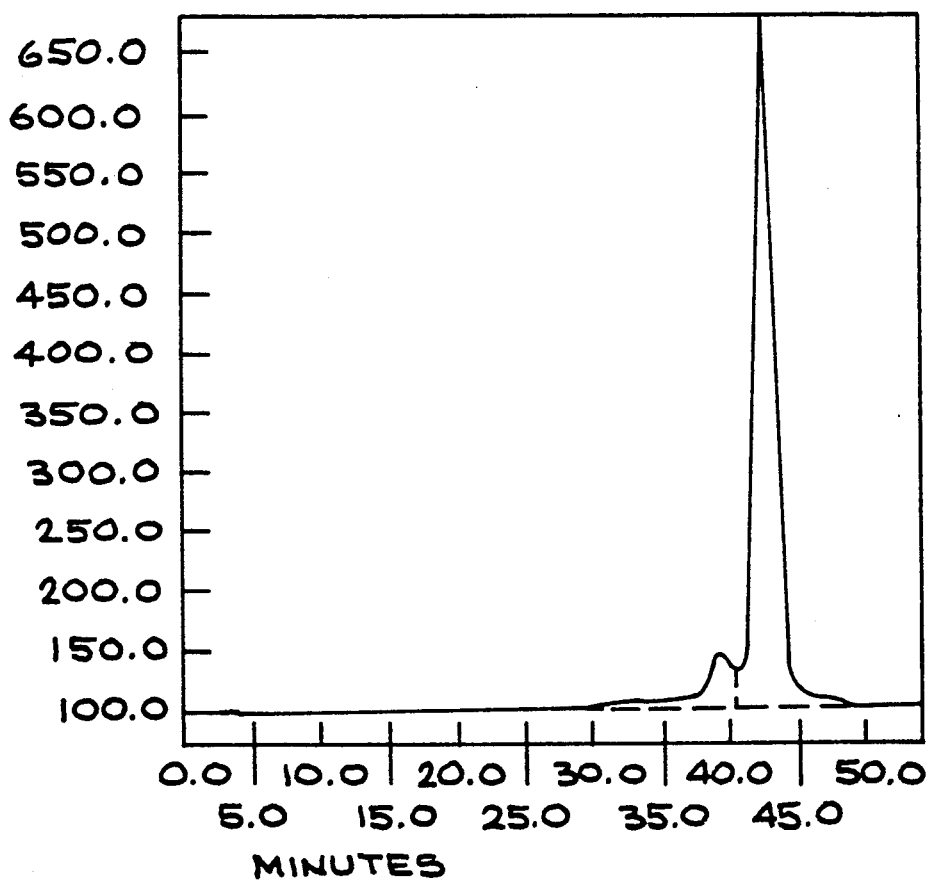

FIG. 1e is a chromatogram of compound (4):

S-d($C_{13}G_3T_4$).

Sulfurization steps were carried out with 3H-1,2-benzothiol-3-one 1,1-dioxide, as described by Iyer et al (cited above). The 5'-O-dimethoxytrityl derivatives of the crude DNA from each synthesis was initially purified by reversed-phase preparative chromatography as described by Zon et al, Biochromatography, Vol. 1, pg. 22 (1988).

Analytical separation of the completely sulfurized and incompletely sulfurized phosphorothioate oligonucleotides was carried out on a Perkin-Elmer Series 410 B10 liquid chromatography system using a Perkin-Elmer ISS-200 Autosampler, a Perkin-Elmer Model 1020 Data System, and an Applied Biosystems, Inc. Model 759A UV detector. The column was 15 cm×7.5 mm i.d. loaded with a quaternary alkylammonium functionalized support, Polymer Labs PL-SAX, with particle size of 10 $\mu$m and pore size of 1000 angstroms. The buffer solution consisted of three components: A (50 mM ammonium phosphate buffer pH 8.2 and acetonitrile in a 95:5 ratio (v/v)); B (1.5M potassium bromide in 50 mM ammonium phosphate buffer pH 6.7 and acetonitrile in an 80:20 ratio (v/v)); and C (acetonitrile). The concentration of the bromide soft-base counter ion was brought linearly from 0.45M to 1.2M in 48 minutes by going from 50A:30B:20C to 0A:80B:20C. The flow rate was 1.5 ml/min and the eluted material was detected by UV absorbance at 260 nm. FIGS. 1 a-e are the resulting chromatograms of compound 1, 2 (high O), 2 (low O), 3, and 4 respectively. The roman numerals above the peaks correspond to the roman numerals in the Tables I and II.

DETAILED DESCRIPTION OF THE INVENTION

Mixtures of completely sulfurized and incompletely sulfurized phosphorothioate or phosphorodithioate oligonucleotides for use in the method of the invention can arise from all currently available methods of synthesizing phosphorothioate and phosphorodithioate oligonucleotides. Detailed procedures for the phosphoramidite, phosphorthioamidite, and hydrogen phosphonate methods of oligonucleotide synthesis are described in the following references, which are incorporated by reference: Caruthers et al, U.S. Pat. Nos. 4,458,066 and 4,500,707; Koester et al, U.S. Pat. No. 4,725,677; Matteucci et al, *J. Amer. Chem. Soc.,*Vol. 103, pgs. 3185-3191 (1981); Caruthers et al, *Genetic Engineering,* Vol. 4, pgs. 1-17 (1981); Jones, chapter 2, and Atkinson et al, chapter 3, in Gait, ed., *Oligonucleotide Synthesis: A Practical Approach* (IRL Press, Washington, D.C., 1984); Froehler et al, *Tetrahedron Letters,* Vol. 27, Pgs. 469-472 (1986); Garegg et al, *Tetrahedron Letters,* Vol. 27, pgs. 4051-4054 and 4055-4058 (1986); Andrus et al, U.S. Pat. No. 4,816,571; Brill et al, J. Am. Chem. Soc., Vol. 111, pgs. 2321- (1989); and Froehler et al, *Nucleic Acids Research,* Vol. 14, pgs. 5399-5407 (1986). Various sulfurization methods are disclosed by Matsukura et al, Gene (cited above); Iyer et al, J. Org. Chem., Vol. 55, pgs. 4693–4699 (1990); Hirschbein, U.S. patent application Ser. No. 07/464,182 and Stec et al, U.S. patent application Ser. No. 07/512,644.

Preferably, the methods of the invention are implement by high performance, or high pressure, liquid chromatography (HPLC). Extensive guidance for choosing particular design parameters, e.g. column size, flow rates, strong anion exchanger (both matrix and covalently attached cationic group), and the like, is available in any of many texts on liquid chromatography, e.g. Snyder and Kirkland, Introduction to Modern Liquid Chromatography, 2nd Ed. (Wiley Interscience, New York, 1979).

A variety of strong anion exchangers can be used, but preferably the exchanger matrix must be suitable for use in HPLC. For example, it must be mechanically rigid, stable under oridinary operating pressures, inert with respect to the solvents employed, stable in the pH range employed, and the like. Preferably, highly cross-linked styrene-divinylbenzene matrices are preferred that are derivatized with quaternary alkylammonium cations, such as triethylaminoethyl, diethyl-(2-hydroxypropyl-)aminoethyl, and the like.

The particle size is an important factor in determining how well the completely and incompletely phosphorothioate oligonucleotides are resolved as separate peaks in the chromatographic process. Preferably, the particle size is less than about 15 μm diameter, and more preferably, particle size is in the range of about 8–10 μm. The porosity of the ion exchange resin is not critical. Pore size in the range of 60 to 1000 angstroms is suitable.

The temperature considerations of the process are similar to those of any ion exchange process. The appropriate operating temperature will thus depend on the volume of the exchanger in the column, the particle size, the surface area and other similar variables and can be readily determined by routine experimentation. It will be most convenient to operate at a temperature within the range of about 14° C. to about 35° C., preferably from about 17° C. to about 30° C., and most preferably, from about 20° C. to about 28° C.

The buffer solution is a liquid medium in which counter ions are delivered to the adsorbed sample at a controlled concentration and pH. Optionally, the buffer solution may contain one or more organic modifiers to assist in the desorption process. Preferably, organic modifiers are included in the buffer solution (1) to ensure that the oligonucleotides in the sample remain single stranded, and (2) to neutralize hydrophobic interactions between the oligonucleotides and support matrix. Furthermore, to avoid interference with the detection of the eluted oligonucleotides, the organic modifier can only absorb light in the wavelength range of 250–280 nm. Preferable organic modifiers include acetonitrile, formamide, urea, and like solvents. Most preferably, acetonitrile is used as an organic modifier.

The pH is optimized for a particular soft-base counter ion. Likewise, the concentration gradient of the soft-base counter ion, including functional shape, time course, and the like, are selected to optimize separation and can be readily determined by routine experimentation taking into account column size, flow rates, amount of adsorbed sample, and the like. Preferably, the concentration of the soft-base counter ion is increased monotonically until the sample desorbing concentration is reached, after which the concentration is held substantially constant for a time long enough to remove substantially all the completely sulfurized phosphorothioate oligonucleotide. Finally, the cycle is completed by returning the concentration to the starting value.

The volume and flow rate of the buffer solution to be passed through the exchanger bed will be selected to provide the optimum separation and, as before, can be determined by routine experimentation.

When the method of the invention is used analytically, fractions of the compounds having full or partial sulfurization are readily determined by comparing chromatogram peak areas with the total area under all peaks.

EXAMPLE

In this example four phosphorothioate oligonucleotides were synthesized and completely sulfurized and incompletely sulfurized components were separated in accordance with the invention. The fractions of completely sulfurized and incompletely sulfurized components were confirmed by NMR analysis. The following phosphorothioate oligonucleotides were synthesized via phosphoramidite chemistry on either an Applied Biosystems Model 380B or 390Z automated DNA Synthesizer using standard protocols, e.g. citations above and Efcavitch, pg. 221 in Schlesinger, ed. Macromolecular Sequencing and Synthesis: Selected Methods and Applications (Alan R. Liss, New York, 1988): S-$d(C_{12}G_5T_{10})$ (1), S-$d(A_3C_7G_7T_4)$ (2), S-$d(A_1C_8G_2T_9)$ (3), and S-$d(C_{13}G_3T_4)$ (4), wherein (for example) $d(C_{12}G_5T_{10})$ represents a 27-mer oligodeoxyribonucleotide 5'-CCCCCCCCCCCCGGGGGTTTTTTTTTT and the prefix "S-" indicates that the phosphodiester linkages have been sulfurized. Sulfurization steps were carried out with 3H-1,2-benzothiol-3-one 1,1-dioxide, as described by Iyer et al (cited above). The 5'-O-dimethoxytrityl derivatives of the crude DNA from each synthesis was initially purified by reversed-phase preparative chromatography as described by Zon et al, Biochromatography, Vol. 1, pg. 22 (1988).

Analytical separation of the completely sulfurized and incompletely sulfurized phosphorothioate oligonucleotides was carried out on a Perkin-Elmer Series 410 B10 liquid chromatography system using a Perkin-Elmer ISS-200 Autosampler, a Perkin-Elmer Model 1020 Data System, and an Applied Biosystems, Inc. Model 759A UV detector. The column was 15 cm×7.5 mm i.d. loaded with a quaternary alkylammonium functionalized support, Polymer Labs PL-SAX, with particle size of 10 μm and pore size of 1000 angstroms. The buffer solution consisted of three components: A (50 mM ammonium phosphate buffer pH 8.2 and acetonitrile in a 95:5 ratio (v/v)); B (1.5M potassium bromide in 50 mM ammonium phosphate buffer pH 6.7 and acetonitrile in an 80:20 ratio (v/v)); and C (acetonitrile). The concentration of the bromide soft-base counter ion was brought linearly from 0.45M to 1.2M in 48 minutes by going from 50A:30B:20C to 0A:80B:20C. The flow rate was 1.5 ml/min and the eluted material was detected by UV absorbance at 260 nm. FIGS. 1 a-e are the resulting chromatograms of compound 1, 2 (high O), 2 (low O), 3, and 4 respectively. The roman numerals above the peaks correspond to the roman numerals in the Tables below.

Peaks I, II, and III of compounds 1 and 2 were preparatively isolated and examined by NMR. The preparative isolation was carried out by dissolving about 15 mg of DNA (prepared as described above) in 2 ml of water and transferring to the same column as described above via a loop-injector (Rheodyne 9125). The buffer solution and gradient were the same as above, except that the gradient cycle was 70 min. Fractions consisting of 2-12 mg of each peak were collected, individually desalted, and taken up in $D_2O$ for $^{31}P$-NMR analysis. NMR analysis was carried out on either a JEOL GSX-500 with sampling frequency of 202.45 MHz, acquisition time of 0.655 s, pulse delay of 6 s, and pulse width of 5 us (45°) or a Varian Unity 3000 with sampling frequency of 121.42 MHz, acquisition time of 1-6 s, pulse delay of 0 s, and pulse width of 11 $\mu$s (90°). Table I compares the NMR-determined percentage of unsulfurized phosphodiester linkages in the components corresponding to peaks I-IV of compounds 1 and 2. It is readily seen that the theoretical values (obtained from the binomial distribution) and the measured values are very close.

TABLE I

Percentage of unsulfurized phosphodiester linkages in peaks I-IV of compounds 1 and 2

| | COMPOUND | | | |
|---|---|---|---|---|
| | Found by NMR | | Theoretical | |
| Peak | 1 | 2 | 1 | 2 |
| I | 0.0 | 0.1 | 0.0 | 0.0 |
| II | 5.1 | 3.6 | 3.8 | 5.0 |
| III | 8.8 | 7.7 | 7.7 | 10.0 |
| IV | N.D. | N.D. | 11.5 | 15.0 |

Finally, the fractions of 0-, 1-, 2-, and 3-fold oxygenated components of compounds 1-4 were determined by the method of the invention and compared to theoretical fractions (calculated from the binomial distribution) and the total percent P=S as determined by NMR analysis. The results are displayed in Table II. The multiple entries for the same compound represent separate syntheses of the same compound, which in some cases were sulfurized less efficiently than others.

TABLE II

Total percentage P=S by NMR and percentage of 0-, 1-, 2-, and 3-fold oxygenated components of compounds 1-4 by HPLC (Exp) and theory (Calc)

| | | Peak I | | Peak II | | Peak III | | Peak IV | |
|---|---|---|---|---|---|---|---|---|---|
| Compound | NMR | Calc | Exp | Calc | Exp | Calc | Exp | Calc | Exp |
| 1 | 99.3 | 83.3 | 83.7 | 15.3 | 14.1 | 1.35 | 1.9 | .07 | 0.3 |
| 1 | 98.3 | 64.0 | 64.5 | 28.8 | 29.0 | 6.2 | 5.6 | 0.9 | 0.8 |
| 1 | 98.0 | 59.1 | 58.1 | 31.4 | 29.4 | 8.0 | 9.8 | 1.3 | 2.7 |
| 2 | 99.6 | 92.3 | 90.0 | 7.4 | 7.9 | 0.3 | <2 | <<0.1 | <0.5 |
| 2 | 97.3 | 57.8 | 52.4 | 32.1 | 33.5 | 8.5 | 11.3 | 1.4 | 2.8 |
| 3 | 99.7 | 94.4 | 93.8 | 5.4 | 5.9 | <0.2 | <0.5 | <0.1 | <0.5 |
| 4 | 99.7 | 94.4 | 93.0 | 5.4 | 7.0 | <0.2 | <0.5 | <0.1 | <0.5 |

What is claimed is:

1. A method of separating completely sulfurized phosphorothioate or phosphorodithioate oligonucleotides from a mixture of completely sulfurized and incompletely sulfurized phosphorothioate or phosphorodithioate oligonucleotides, the method comprising the steps of:
    (a) impregnating a strong anion exchanger with the mixture of completely sulfurized and incompletely sulfurized phosphorothioate or phosphorodithioate oligonucleotides, the strong anion exchanger consisting of a mechanically rigid styrene-divinylbenzene matrix derivatized with a quaternary alkylammonium cation;
    (b) passing through the strong anion exchanger a buffer solution comprising a a soft-base counter ion at a concentration which monotonically increases with time to a sample-desorbing concentration, the soft-base counter ion being selected from the group consisting of bromide, thiocyanate, azide, iodide, and sulfide; and
    (d) recovering the eluate from step (b).

2. The method of claim 1 wherein said soft-base counter ion is selected from the group consisting of bromide and thiocyanate.

3. The method of claim 2 wherein said buffer solution comprises a soft-base counter ion at a concentration which increases linearly with time to said sample-desorbing concentration.

4. A method of measuring the fraction of completely sulfurized phosphorothioate or phosphorodithioate oligonucleotides in a mixture of completely sulfurized and incompletely sulfurized phosphorothioate or phosphorodithioate oligonucleotides, the method comprising the steps of:
    (a) impregnating a strong anion exchanger with the mixture of completely sulfurized and incompletely sulfurized phosphorothioate or phosphorodithioate oligonucleotides, the strong anion exchanger consisting of a mechanically rigid styrene-divinylbenzene matrix derivatized with a quaternary alkylammonium cation;
    (b) passing through the exchanger a buffer solution comprising a soft-base counter ion at a concentration which monotonically increases with time to a sample-desorbing concentration so that a chromatogram of the eluted completely sulfurized and incompletely sulfurized phosphorothioate and phosphorodithioate oligonucleotides is formed, the soft-base counter ion being selected from the group consisting of bromide, thiocyanate, azide, iodide, and sulfide; and
    (c) computing the ratio of the peak area corresponding to the completely sulfurized phosphorothioate or phosphorodithioate oligonucleotide on the chromatogram to the total area under all peaks corresponding to both completely sulfurized and incompletely sulfurized phosphorothioate or phosphorodithioate oligonucleotides on the chromatogram.

5. The method of claim 4 wherein said soft-base counter ion is selected from the group consisting of bromide and thiocyanate.

6. The method of claim 5 wherein said buffer solution comprises a soft-base counter ion at a concentration which increases linearly with time to said sample-desorbing concentration.

* * * * *